United States Patent
Fisher et al.

(10) Patent No.: US 6,187,819 B1
(45) Date of Patent: Feb. 13, 2001

(54) PROTEIN KINASE C ACTIVATORS AND THEIR USE IN DECREASING EXPRESSION OF CELL ANTIGENS

(75) Inventors: Paul B. Fisher, Scarsdale, NY (US); Jorge A. Leon, Tenafly, NJ (US)

(73) Assignee: The Trustees of Columbia University in the City of New York, New York, NY (US)

(*) Notice: Under 35 U.S.C. 154(b), the term of this patent shall be extended for 0 days.

(21) Appl. No.: 08/619,777

(22) PCT Filed: Sep. 21, 1994

(86) PCT No.: PCT/US94/10755

§ 371 Date: Jun. 10, 1996

§ 102(e) Date: Jun. 10, 1996

(87) PCT Pub. No.: WO95/08326

PCT Pub. Date: Mar. 30, 1995

Related U.S. Application Data

(63) Continuation-in-part of application No. 08/124,716, filed on Sep. 21, 1993, now Pat. No. 5,681,860.

(51) Int. Cl.[7] ........................ A61K 31/16; A61K 31/355; A61K 31/21
(52) U.S. Cl. ........................ 514/629; 514/463; 514/510; 549/432; 554/63; 560/174; 564/223
(58) Field of Search ................................ 564/233; 554/63; 560/174; 549/432; 514/629, 510, 463

(56) References Cited

PUBLICATIONS

Barton, K., et al (1989) "The effects of the Antitumor agent mazerein on the cytotoxic capacity and oxidative metabolism of human blood cells." *Chemical Abstracts* 111: abstract No. 146415w, *Invest. New Drugs* (1989) 7: 79–188 (Exhibit B).*

Celada, A. and Maki, R.A. (1991) "IFN–γ induces the expression of the genes for MHC Class II I–A$_\beta$ and tumor necrosis factor through a protein kinase C–independent pathway." *J. Immunol*. 146:114–120.*

Downey, G.P., et al. (1992) "Phorbol ester–induced actin assembly in neutrophils: role of protein kinase C." *J. Cell Biol.* 116:695–706.*

Fisher, P.B. and Rowley, P.T. (1991) "Regulation of growth, differentiation and antigen expression in human tumor cells by recombinant cytokines: potential applications for the differentiation therapy of human cancer." *In*: Waxam, S., Rossi, B.B., and Takaku, F. (eds.) *Status of differentiation therapy of cancer*, vol. II Raven Press, New York, pp. 201–213.*

Fuith, L.C., et al. (1991) "Enhancement of CA 125 expression by interferon–gamma in ovarian carcinoma xenografts." *J. Tumor Marker Oncology* 6: 85–89.*

Giacomini, P., et al. (1984) "Modulation by recombinant DNA leukocyte (α) and fibroblast (β) interferons of the expression and shedding of HLA—and tumor–associated antigens by human melanoma cells." *J. Immunol.* 133: 1649–1655.*

Greiner, J.W., et al. (1984) "Enhanced expression of surface tumor–associated antigens on human breast and colon tumor cells after recombinant human leukocyte α–interferon treatment." *Cancer Res.* 44:3208–3213.*

Greiner, J.W., et al. (1986) "Differential effects of recombinant human leukocyte interferons on cell surface antigen expression," *Cancer Res.* 46:4894–4990.*

Harada, Y., et al. (1993) "Tumor differentiation and immunohistochemical markers in adenocarcinoma." *Chemical Abstracts* 118: abstract No. 57252t, *Wakayama Igaku* (1991) 42:759–765 (Exhibit C).*

Leon, J.A., et al. (1992) "Modulation of the antigenic phenotype of human breast carcinoma cells by modifiers of protein kinase C activity and recombinant human interferons." *Cancer Immunology Immunotherapy* 35: 315–324.*

Murray, J.L., et al. (1990) "Recombinant α–interferon enhances tumor targeting of an antimelanoma monoclonal antibody in vivo." *J. Biol. Resp. Mod.* 9: 556–563.*

Reddy L.L., et al. (1990) "Evidence that weak promotion of carcinogen–initiated cells prevents their progression to malignancy." *Carcinogenesis* 11: 2123–2126.*

Wender, P.A., et al. (1986) "Analysis of the phorbol ester pharmacophore on protein kinase C as a guide to the rational design of new classes of analogs." *Proc. Natl. Acad. Sci.* (USA) 83:4214–4218.*

* cited by examiner

*Primary Examiner*—Peter O'Sullivan
(74) *Attorney, Agent, or Firm*—John P. White; Cooper & Dunham

(57) ABSTRACT

A composition for the upregulation of expression of cell antigens, without inducing shedding, which comprises a protein kinase C activator is provided by this invention. Further provided by this invention is a method of detecting and treating tumor cells comprising contacting tumor cells with an effective amount of a protein kinase C activator for the upregulation of expression of antigens of tumor cells, without inducing antigen shedding, and detecting the presence of said antigen or then further contacting said tumor cells with an effective amount of an antibody directed to said antigen.

10 Claims, 3 Drawing Sheets

PROTEIN KINASE C ACTIVATORS AND THEIR USE IN DECREASING EXPRESSION OF CELL ANTIGENS

This is a national application based on PCT International Application PCT/US94/10755, filed Sep. 21, 1994 which is a continuation-in-part of U.S. Ser. No. 08/124,716 filed Sep. 21, 1993, now U.S. Pat. No. 5,681,680, the contents of which are hereby incorporated in their entirety.

The invention described herein was made in the course of work under Grant Nos. CA 35675 and CA 43208 from the National Institute of Health-National Cancer Institute. The United States Government has certain rights in this invention.

BACKGROUND OF THE INVENTION

Throughout this application, various publications are referenced by Arabic number within brackets. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed therein.

The expression of both histocompatibility antigens and tumor associated antigens (TAAs) of tumor cells can be augmented by treatment with bioresponse modulators, such as interferon and tumor necrosis factor-$\alpha$, and phorbol ester tumor promoters, such as TPA [1,13,14,16,18,22,23,27,28]. Upregulation of additional cellular antigens can be induced to a similar extent in both normal and tumor cells by bioresponse modulators indicating that this effect is a general property of these compounds and not restricted to TAAs or cells of a specific histotype (for review see [1,23]). For example, various interferons have been shown to enhance the expression of histocompatibility antigens, cellular antigens and TAAs in breast carcinoma, central nervous system tumors, colon carcinoma and melanoma cells [21–23,27,28,31,38]. In addition, when administered to animals containing human tumor xenografts, recombinant human interferon augments the ability of excised tumors to bind monoclonal antibodies specific for TAAs [13,21,36,42]. The use of bioresponse modifiers for increasing the expression of TAAs by tumor cells may prove useful in reducing the antigenic heterogeneity in tumors in vivo and augmenting the ability of monoclonal antibodies to bind to tumors (for review see [1,23,25,26]).

TPA and recombinant human leukocyte (IFN-$\alpha$), fibroblast (IFN-$\beta$) and immune (IFN-$\gamma$) interferons increase both the expression and shedding of the tumor associated antigen BCA 225 by T47D cells and MCF-7 human breast carcinoma cells [36]. These compounds also increase the expression of the TAA carcinoembryonic antigen (CEA) and HLA Class II-DR antigen in both T47D and MCF-7 cells [20,36]. The mechanism by which TPA induces its diversity of effects in target cells is believed to be mediated initially by its binding to the $Ca^{2+}$-activated and phospholipid-dependent enzyme PKC which is the high affinity receptor for TPA (for review see [10, 43,44]). As a consequence of activation of PKC many important biochemical processes are initiated in target cells, including both positive and negative feedback controls in signal transduction pathways (for review see [43,44]). Recent studies have implicated PKC activation in mediating both antiviral activity and specific gene regulatory changes induced by IFN-$\alpha$, IFN-$\beta$, and IFN-$\gamma$ [6,8,37,46,47,50] and for review see [9]. The purpose of the present study was to explore the possible relationship between PKC activation and antigen upregulation induced by phorbol esters and interferon. With this aim in mind applicants have determined the effect of the synthetic PKC-activator ADMB, the natural PKC activators TPA and MEZ and the combination of PKC-activators and the PKC-inhibitor H-7 on the antigenic phenotype of T47D cells. To determine if similar biochemical pathways are involved in the ability of IFN-$\beta$ and IFN-$\gamma$ to alter the antigenic phenotype of T47D cells, applicants have also evaluated the effect of H-7 on interferon upregulation of the same antigens in T47D cells.

The effect of a synthetic protein kinase C (PKC) activator 3-(N-acetylamino)-5-(N-decyl-N-methylamino)-benzyl alcohol (ADMB) and the natural PKC-activating tumor promoting agents 12-0-tetradecanoyl-phorbol-13-acetate (TPA) and mezerein (MEZ) on the antigenic phenotype of carcinoma cells was studied. All three agents increased the surface expression of the tumor associated antigen such as BCA 225 and also of various cellular antigens, including HLA Class II antigens, intercellular adhesion molecule-1 (ICAM-1) and c-cerbB-2. Expression of the same antigens was also upregulated to various extent in T47D cells by recombinant fibroblast (IFN-$\beta$) and immune (IFN-$\gamma$) interferon. Shedding of BCA 225 from T47D cells was induced by TPA, MEZ, IFN-$\beta$ and IFN-$\gamma$, whereas ADMB did not display this activity. The ability of ADMB, TPA and MEZ to modulate the antigenic phenotype of T47D cells appears to involve a PKC-mediated pathway, since the PKC inhibitor, H-7, eliminates antigenic modulation. In contrast, the ability of IFN-$\beta$ and IFN-$\gamma$ to enhance HLA Class II antigens, c-erbB-2 and ICAM-1 expression, was either unchanged or modestly reduced by simultaneous exposure to H-7. Analysis of steady-state mRNA levels for HLA Class I antigens, HLA Class II-DR$\beta$ antigen, ICAM-1, and c-erbB-2 indicated that the ability of H-7 to inhibit expression of these antigens in TPA-, MEZ-, and ADMB-treated cells was not a consequence of a reduction in the steady-state levels of mRNAs for these antigens. The results of the present investigation indicate that the biochemical pathways mediating enhanced antigenic expression in T47D cells induced by TPA, MEZ and the synthetic PKC activator ADMB are different than those induced by recombinant interferons. Furthermore, upregulation of antigenic expression in T47D cells can occur by both a PKC-dependent or a PKC-independent pathway.

SUMMARY OF THE INVENTION

This invention provided a composition for the upregulation of expression of all antigens without inducing shedding which comprises a protein kinase C activation for the upregulation of expression of a cell antigen without inducing shedding of said antigen from the cell.

Further provided by this invention is a method for decreasing tumor cell heterogeneity by upregulating the expression of an antigen without inducing shedding of said antigen which comprises administering an amount of a protein kinase C activator to cells to induce upregulation of expression of an antigen without inducing shedding of said antigen.

Additionally, this invention provides a method of detecting tumor cells comprising contacting tumor cells with an effective amount of a protein kinase C activator for the upregulation of expression of antigens of tumor cells, without inducing shedding, and detecting the presence of said antigen.

A method for treating tumor cells is also provided. This method comprises contacting tumor cells with an effective amount of a protein kinase C activator for the upregulation of expression of antigens of tumor cells without inducing antigen shedding and then contacting said tumor cells with an effective amount of an antibody directed to said antigen.

This invention also provides a pharmaceutical composition for upregulating the expression of antigens without inducing antigen shedding which comprises a pharmaceutically acceptable carrier and an effective amount of a protein kinase C activator.

DETAILED DESCRIPTION OF THE INVENTION

Figure 1A:
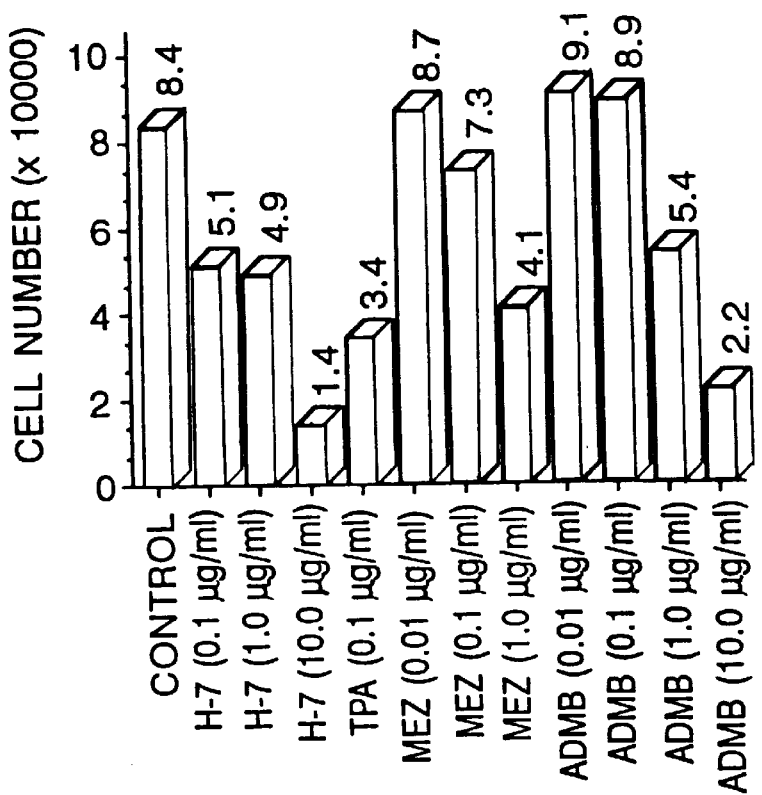
FIG. 1: Effect of H-7, TPA, MEZ and ADMB on T47D cell growth and DNA synthesis. Cell growth assays are presented in (A). T47D cells were seeded at $1 \times 10^4$ cells/35 mm tissue culture place, the medium was changed with the indicated compounds 24 hr later and cell numbers were determined after an additional 72 hr growth at 37° C. by Coulter Counter. Results are the average of triplicate samples/experimental condition which varied by $\leq 10\%$. DNA synthesis assays are presented in (B). T47 D cells were seeded at $1.25 \times 10^4$ cells in 0.2 ml of media in 96 microtiter plates. Every 24 hr, cultures received 1 $\mu$Ci of methyl-$^3$H-thymidine and 8 hr later cells were harvested and TCA precipitable counts were determined. Results are the average from replicate samples exposed to the indicated compounds for 72 hr. Replicate samples varied by $\leq 10\%$ and replicate studies varied by $\leq 15\%$. Further details can be found in "Detailed Description Of The Invention".

This invention provides a composition for the upregulation of expression of cell antigens without inducing shedding which comprises a protein kinase C activator for the upregulation of expression of a cell antigen without inducing shedding of said antigen from the cell. In one embodiment of the invention the protein kinase C activator is a synthetic protein kinase C activator. In the preferred embodiment of the invention the protein kinase C activator is 3-(N-acetylamino)-5-(N-decyl-N-methylamino)-benzyl alcohol (ADME).

In an embodiment of the invention the cell antigen is a tumor associated antigen (TAA). In yet another embodiment of the invention the cell antigen is a cell surface antigen. The cell antigen may also be a histocompatibility antigen. Examples of tumor associated antigens that can be upregulated by this invention include, but are not limited to, BCA 225, c-erb B2, carcinoembryonic antigen or CA19.9. In one preferred embodiment of the invention the cell surface antigen is intercellular adhesion molecule-1.

The tumor of the tumor associated antigen may be, but is not limited to, breast carcinoma or colon carcinoma.

In an embodiment of the above-described composition, the tumor of the tumor associated antigen is a colon carcinoma. In a further embodiment, the colon carcinoma associated antigen is a histocompatibility antigen. In a still another embodiment, the histocompatibility antigen is Class II HLA-DR. In another embodiment, the colon carcinoma associated antigen is CA19.9.

Further provided by this invention is a method for decreasing tumor cell heterogeneity by upregulating the expression of an antigen without inducing shedding of said antigen which comprises administering an amount of a protein kinase C activator to cells to induce upregulation of expression of an antigen without inducing shedding of said antigen. In one embodiment of the invention the protein kinase C activator is a synthetic protein kinase C activator. In a preferred embodiment of the invention the synthetic protein kinase C activator is 3-(N-acetylamino)-5-(N-decyl-N-methylamino)-benzyl alcohol (ADMB). When using ADMB for decreasing tumor cell heterogeneity by upregulating the expression of an antigen, without inducing shedding, the effective amount is from about 0.01 $\mu$g/ml to about 10 $\mu$g/ml.

In one embodiment of the invention the antigen is a tumor associated antigen. In another embodiment of the invention the antigen is a histocompatibility antigen. In yet another embodiment of the invention the antigen is a cell surface antigen. The tumor of the tumor associated antigen can be, but is not limited to, breast carcinoma or colon carcinoma. In certain embodiments of the invention the tumor associated antigen is BCA 225. In other embodiments of the invention the tumor associated antigen is carcinoembryonic antigen. In yet another embodiment of the invention the tumor associated antigen is c-erb B2. In another embodiment of the invention the cell surface antigen in intercellular adhesion molecule-1.

In a further embodiment, the colon carcinoma associated antigen is a histocompatibility antigen. In a still another embodiment, the histocompatibility antigen is Class II HLA-DR. In another embodiment, the colon carcinoma associated antigen is CA19.9.

This invention also provides a method of detecting tumor cells comprising contacting tumor cells with an effective amount of a protein kinase C activator for the upregulation of expression of antigens of tumor cells, without inducing antigen shedding, and detecting the presence of said antigen. In one embodiment of the invention the protein kinase C activator is a synthetic protein kinase C activator. In the preferred embodiment of the invention the synthetic protein kinase C activator is 3-(N-acetylamino)-5-(N-decyl-N-methylamino)-benzyl alcohol (ADMB). When using ADMB in the subject invention the effective amount is from about 0.01 μg/ml to about 10 μg/ml. The tumor of the tumor associated antigen may be, but is not limited to, breast carcinoma or colon carcinoma. In certain embodiments of the invention the tumor associated antigen is BCA 225. The tumor associated antigen can also be carcinoembryonic antigen or c-erb B2. In yet another embodiment of the invention the antigen is intercellular adhesion molecule-1.

In a further embodiment, the colon carcinoma associated antigen is a histocompatibility antigen. In a still another embodiment, the histocompatibility antigen is Class II HLA-DR. In another embodiment, the colon carcinoma associated antigen is CA19.9.

Further provided by this invention is a method of treating tumor cells comprising contacting tumor cells with an effective amount of a protein kinase C activator for the upregulation of expression of antigens of tumor cells without inducing antigen shedding and then contacting said tumor cells with an effective amount of an antibody directed to said antigen. In one embodiment of the invention the protein kinase C activator is a synthetic protein kinase C activator. In the preferred embodiment of the invention the synthetic protein kinase C activator is 3-(N-acetylamino)-5-(N-decyl-N-methylamino)-benzyl alcohol (ADMB). When using ADMB, the effective amount is from about 0.1 μg/ml to about 10 μg/ml. The antigen may be, but is not limited to, a tumor associated antigen or a cell surface antigen. The tumor cells may be, but are not limited to, breast carcinoma or colon carcinoma. In preferred embodiments of the invention the tumor associated antigen is BCA 225, carcinoembryonic antigen, or c-erb B2. In yet another embodiment of the invention the cell surface antigen is intercellular adhesion molecule-1.

In a further embodiment, the colon carcinoma associated antigen is a histocompatibility antigen. In a still another embodiment, the histocompatibility antigen is Class II HLA-DR. In another embodiment, the colon carcinoma associated antigen is CA19.9.

Additionally, this invention provides a pharmaceutical composition for upregulating the expression of antigens without inducing antigen shedding which comprises a pharmaceutically acceptable carrier and an effective amount of a protein kinase C activator. In one embodiment of the invention the protein kinase C activator is a synthetic protein kinase C activator. In the preferred embodiment of the invention the synthetic protein kinase C activator is 3-(N-acetylamino)-5-(N-decyl-N-methylamino)-benzyl alcohol (ADMB). When the protein kinase C activator is ADMB, the effective amount is from about 0.01 μg/ml to about 10 μg/ml. The antigen may be, but is not limited to being, a tumor associated antigen, a cell surface antigen, or histocompatibility antigen. The tumor of the tumor associated antigen may be, but is not limited to, breast carcinoma or colon carcinoma. In one embodiment of the invention the tumor associated antigen is ECA 225. In another embodiment of the invention the tumor associated antigen is carcinoembryonic antigen. In yet another embodiment of the invention the tumor associated antigen is c-erb B2. In one embodiment of the invention the cell surface antigen is intercellular adhesion molecule-1.

In a further embodiment, the colon carcinoma associated antigen is a histocompatibility antigen. In a still another embodiment, the histocompatibility antigen is Class II HLA-DR. In another embodiment, the colon carcinoma associated antigen is CA19.9.

For the purposes of this invention, "physiologically acceptable carrier" means any of the standard pharmaceutical carriers. Examples of suitable carriers are well known in the art and may include, but are not limited to, any of the standard pharmaceutical carriers.

Methods of determining the effective amounts are well known in the art. A person of ordinary skill in the art can easily extrapolate the effective amounts as determined in vitro, and apply it to living organisms to determine the effective concentrations in vivo.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Materials and Methods Cell Cultures

The T47D clone 11 human breast carcinoma cell line [32] was grown in RPMI 1640 medium supplemented with 2mM L-glutamine, 1 mM sodium pyruvate, fungizone (0.25 μg/ml), streptomycin (50 μg/ml), penicillin (50 U/ml), 10% fetal bovine serum (FBS), β-estradiol and insulin (0.1 μu/ml) at 37° C. in a 5% $CO_2$/95% air humidified incubator. Cultures were maintained in the logarithmic phase of growth by subculturing at a 1:5 or 1:10 split-ratio when cells approached confluency.

Growth and $^3$H-Thymidine Incorporation Assays

T47D cells were seeded at $5 \times 10^3$ cells/ml in 35 mm tissue culture plates and 24 hr later the medium was changed with the indicated compounds. Seventy-two hr later the cells were resuspended in trysin/versene (0.125%/0.02%, w/w) and counted using a $Z_M$ Coulter Counter (Coulter Electronics). For $^3$H-thymidine incorporation studies, T47D cells were seeded at $1.25 \times 10^4$ cells in 0.2 ml of media in 96 well microtiter plates. Every 24 hr, plates received 1 μCi of methyl-$^3$H-thymidine (specific activity 10 μCi/mmol) (ICN Radiochemicals, Irvine, Calif.), cells were harvested 8 hr after the addition of labeled thymidine and TCA precipitable counts [55] were determined using a Packard scintillation counter. Replicate samples varied by ≦10% and replicate studies varied by ≦15%.

Monoclonal Antibodies $IgG_1$ murine monoclonal antibody Cu18 and Cu46 recognize two different epitopes of a highly restricted breast carcinoma associated glycoprotein of $M_r$ 225,000 to 250,000 (BCA 225) [41]. This TAA is expressed intracytoplasmically and on the membrane of 94% of breast tumors tested and in the T47D human breast carcinoma cell line. BCA 225 is shed into the culture medium by T47D cells and into the sera of breast cancer patients. $IgG_{2a}$ monoclonal antibody L243 (anti HLA Class II-DR) recognizes a monomorphic HLA Class II-DR-α epitope (ATCC M355). Monoclonal antibody CL203.4 [40], which recognizes ICAM-I, was kindly provided by Dr. S. Ferrone, New York Medical College, NY. The c-erbB-2 monoclonal antibody which recognizes the extracellular domain of c-erbB-2 was obtained from Triton Biosciences, Inc., Alamedia, Calif. Monoclonal antibodies Cu18 and Cu46 were used at 0.05 μg/ml and monoclonal antibodies interacting with HLA Class II-DR, ICAM-1 and c-erbB-2 were used at 10 μg/ml. For each experiment, isotype matched control backgrounds (IgG for Cu18, Cu46 and ICAM-1, $IgG_{2a}$ for HLA Class Ii and $IgG_{2b}$ for c-erbB-2) were subtracted from the experimental results. Background from antimouse IgG FITC antibody was also subtracted from experimental results. Applicants never observed backgrounds higher than 2% of total cells for isotypic mouse IgG or higher than 5% for antimouse IgG FITC.

Analysis of TAA and Cellular Antigen Expression by Fluorescence Activated Cell Sorter (FACS) Analysis T47D cells treated with the various compounds were analyzed by flow cytometry using appropriate monoclonal antibody concentrations as described previously [36]. Briefly, $1 \times 10^5$ cells were incubated with the test antibody for 30 min at 4° C., washed 3× with PBS and incubated with a goat α mouse F $(ab)_2$ FITC conjugated test antibody at a 1:40 dilution for 30 min at 4° C. Cells were then washed 3× with PBS and analyzed on a FACStar (Beckon Dickinson, Mountain View, Calif.) or a Coulter Epics IV FACS (Coulter, Hialeah, Fla.). Results are expressed as mean fluorescence intensity (MFI) units which were determined as described previously [36]. MFI=(mean channel fluorescence in fluorescence positive antibody–binding cells×% of fluorescence positive antibody–binding cells)–(mean channel fluorescence in unstained cells×% of fluorescence positive cells in the unstained population). All studies were performed a minimum of three or four times with duplicate samples in each experiment. Replicate samples within individual experiments varied by ≦10% and variation between experiments were generally ≦20%.

Analysis of the Synthesis and Shedding of BCA 225

After appropriate incubation times with the various compounds cell lysates were prepared from T47D cells. Cells were washed 3× in PBS, pH 7.6, pelleted and incubated for 1hr at room temperature in 20 mM Tris HCl, pH 7.4, with PMSF. Cultures were then homogenized with a Teflon homogenizer, centrifuged at 3000 RPM for 10 min at 4° C. and the supernatant was mixed 1:2 with 20 mM Tris-HCl, pH 7.4, containing 0.5% NP40 (Sigma). After 1 hr at 4° C., the mixture was spun at 3000 RPM for 10 min and the supernatant was passed through an EXTRACTIGEL column (Pierce, Ill.) to remove excess detergent. Protein concentration was determined by the BCA micro-method (Pierce, Ill.). BCA 225 levels in cell extracts and supernatants from control and treated T47D cells were quantitated using a double-determinant ELISA assay [4,36]. Briefly, Cu18 monoclonal antibody coated Nunc Immunoplates (Nunc, Denmark) were blocked with 1% BSA (Sigma, RIA Reagent Grade) and incubated with a 1:2 dilution of supernatant in duplicate. Standard values for a partially purified BCA 225 preparation were used at a range of 0 to 10 μg/ml in RPMI 1640 plus 10% FBS (T47D growth medium). After 2 hr incubation and three washings with PBS 0.1% Tween 20 a Cu46 monoclonal antibody conjugated to peroxidase was applied to the plate, incubated for 2 hr, washed 6× in PBS 0.1% Tween 20 and the reaction was developed with 16 ng OPD (Sigma, St. Louis) and 4 μl of 30% $H_2O_2$ in McIlvans buffer, pH 9.6. The plates were read on a Dynatech Elisa reader and a linear standard curve was generated and used to calculate the relative amount of BCA 225 in cell lysates and shed into the culture medium. Results were adjusted to ng BCA 225 per mg of protein, or per $1 \times 10^6$ cells. Replicate samples varied by ≦10% and replicate experiments varied by ≦20%.

RNA Isolation and Northern Blotting Analysis

Steady-state levels of HLA Class I, HLA Class II-$DR_\beta$, c-erbB-2 and ICAM-I mRNA in control and treated T47D cells were determined by Northern blotting analysis of total cytoplasmic RNA probed with appropriate $^{32}P$-labeled gene probes as previously described [3,56]. Northern blots were also probed with a $^{32}P$-labeled glyceraldehyde phosphate dehydrogenase (GAPDH) [12,54] gene probe to verify equal mRNA expression under various experimental conditions. Following hybridization, the filters were washed and exposed for autoradiography. Radioautograms were analyzed by densitometer to determine fold-change in mRNA expression as a result of treatment with the different antigenic modulating agents, with or without cocultivation with H-7.

Reagents

Recombinant human leukocyte (IFN-αA) and immune (IFN-γ) interferons were produced in *Escherichia coli* and purified to homogeneity as previously described. [19,49,53]. These interferons were kindly provided by Dr. Sidney Pestka, UMDNJ-Robert Wood Johnson Medical School, Piscataway, N.J. Recombinant human fibroblast (IFN-β) interferon, with a serine substituted for a cysteine at position 17 of the molecule [39], was supplied by Triton Biosciences Inc., Alameda, Calif. as a lycophilized powder with a concentration of $4.5 \times 10^7$ units/ml. The interferon titers were determined by a cytopathic effect inhibition assay with vesicular stomatitis virus on a bovine kidney cell line (MDBK) or human fibroblast AG-1732 cells[49]. Concentrated stocks of interferons were aliquots, frozen at −80° C., thawed immediately prior to use and diluted to the appropriate concentrations in DMEM supplemented with 5 or 10% FBS. TPA (12-0-tetradecanoyl-phorbol-13-acetate), MEZ (mezerein), and ADMB (3-(N-Acetylamino)-5-(N-Decyl-N-Methylamino)-benzyl alcohol) were obtained from LC Services Corp., Woburn, Mass. Stock solutions of 1 mg/ml (TPA and MEZ) or 10 mg/ml (ADMB) were prepared in dimethylsulfoxide, aliquoted and stored at −20° C. The PKC inhibitor H-7 (1-(5-isoquinolinesulfonyl)-2-methylpiperazine dihydrochloride) (Hidaka et al., 1984) (Sigma) was prepared in distilled $H_2O$ and stored at 4° C. For experiments, aliquots were thawed and dispensed in Dulbecco's modified Eagle's medium (DMEM) containing 5 or 10% FBS to yield appropriate final concentrations. The solvent DMSO at (0.025 to 0.05%) did not alter the growth or antigenic expression of T47D cells.

EXPERIMENTAL RESULTS

Effect of TPA, MEZ and ADMB on Growth and DNA Synthesis in T47D Cells

Figure 1B:
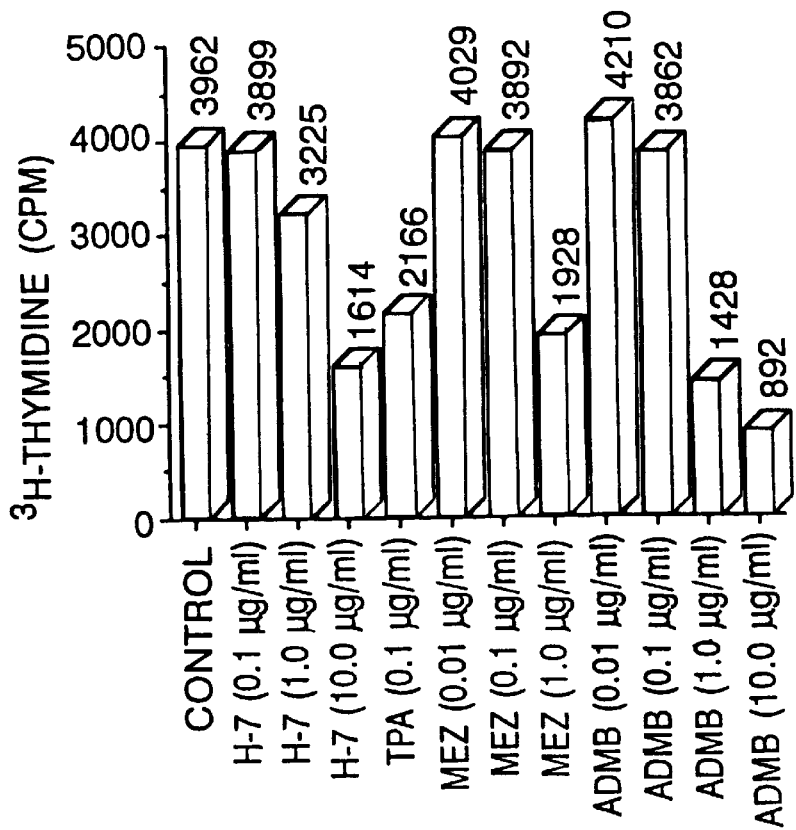

In preliminary studies, the dose-range and time-course of induction of antigenic enhancement in T47D cells by TPA, MEZ and ADMB, as well as the effect of varying doses of H-7 on this process, was determined (data not shown). These studies indicated that the optimum effect on antigenic expression in T47D cells exposed to TPA, MEZ or ADMB occurred by 72 hr. The most effective dose of TPA, MEZ or ADMB inducing upregulation of BCA 225, HLA Class II antigens, ICAM-1 and c-erbB-2 in T47D cells was found to be 0.1 μg/ml. The ability of these PKC activators to induce increased antigenic expression in T47D cells was inhibited by the simultaneous exposure to 0.1 μg/ml of the PKC inhibitor H-7 (Tables 1 and 2). The effect of TPA, MEZ, ADMB and H-7 on 72 hr growth and $^3$H-thymidine incorporation in T47D cells is shown in FIG. 1. When exposed to 0.1 μg/ml of the respective compounds, growth and DNA synthesis was suppressed to the greatest degree in TPA treated cells. In contrast, at the same dose of 0.1 μg/ml, MEZ and ADMB only marginally altered growth and DNA synthesis in T47D cells (FIG. 1). No additive or synergistic effect on 72 hr growth suppression was observed when TPA or MEZ were used in combination with 0.1 μg/ml of H-7 (data not shown).

Effect of TPA, MEZ and ADMB, Alone and in Combination with H-7, on the Antigenic Phenotype of T47D Cells When tested for reactivity with specific monoclonal antibodies, control T47D cells displayed the following constitutive antigenic phenotype: 10 to 20% of cells (with a mean channel fluorescence of 180 to 210) were positive for HLA Class II antigen (HLA-DR) expression; 5 to 10% (with a mean channel fluorescence of 110–130) were positive for c-erbB-2 expression; 80 to 90% (with a mean channel fluorescence of 170 to 200) were positive for ICAM-1 expression; 85 to 95% (with a mean channel fluorescence of 180 to 210) were positive for the TAA BCA 225 (as monitored by the monoclonal antibody Cu18); and 60 to 70% (with a mean channel fluorescence of 140 to 170) were positive for BCA 225 (as monitored by the monoclonal antibody Cu46). The effect of TPA and MEZ, alone and in combination with 0.1 μg/ml of H-7, on HLA Class II antigens, c-erbB-2 and ICAM-1 expression in T47D cells is shown in Table 1. H-7 did not significantly alter the de novo expression of any of these antigens in T47D cells. However, when administered in conjunction with TPA or MEZ, H-7 effectively blocked the ability of these PKC stimulators to enhance antigenic expression. In the experiment shown in Table 1, MEZ was somewhat more effective than TPA in enhancing c-erbB-2 and ICAM-1 expression. An increased activity, at comparable doses, of MEZ over TPA in enhancing the expression of these antigens, as well as the TAA BCA 225, has been found in several additional studies (unpublished data and Table 2 and FIG. 2). For comparison purposes, a single experiment is shown in Table 1. In this experiment, the combination of MEZ+H-7 resulted in the lack of detectable c-erbB-2 expression. This result may reflect technical difficulties rather than a complete suppression in c-erbB-2 expression, since in additional studies H-7 blocked the ability of MEZ to enhance the expression of this antigen without completely eliminating c-erbB-2 expression (unpublished data and FIG. 2).

Recent computer modeling studies have resulted in the synthesis of compounds which inhibit the binding of phorbol esters to PKC and which activate PKC in platelets resulting in the phosphorylation of a specific 40 kDa protein substrate [58]. Applicants have presently tested one of these phorbol ester pharmacophores, ADMB, for its ability to upregulate the same antigens in T47D cells previously shown to be modulated by TPA and MEZ. A comparison of the efficacy of upregulation of HLA Class II antigens and c-erbB-2 in T47D cells exposed to TPA, MEZ and ADMB, in the presence or absence of H-7, is presented in FIG. 2. In the case of HLA Class II antigens, ADMB was somewhat more effective than TPA and MEZ in inducing upregulations, whereas H-7 reduced or eliminated enhancement when applied in combination with these PKC activators. In the case of c-erbB-2, MEZ was the most effective PKC activator tested in enhancing expression and as observed with HLA Class II antigens H-7 reduced this antigenic upregulation.

A series of experiments were conducted to determine the effect of TPA, MEZ and ADMB, alone and in combination with H-7, on the synthesis, surface expression and shedding of the TAA BCA 225 (Table 2). The synthesis of BCA 225 was increased following exposure to all of the PKC activators, with MEZ being most effective in enhancing the synthesis of this TAA. Similarly, MEZ was the most effective of the three PKC activators in enhancing the surface expression of BCA 225 in T47D cells. As observed with the other antigens analyzed, H-7 effectively blocked both the enhanced synthesis and surface expression of BCA 225. When compared for their ability to induce shedding of BCA 225 from T47D cells, a differential response was observed between the three PKC activators (Table 2). Both MEZ and TPA enhance shedding of BCA 225, with MEZ again being more effective than TPA, whereas ADMB did not induce this effect in T47D cells. As observed with both synthesis and shedding, H-7 reduced the ability of MEZ and TPA to induce shedding of BCA 225.

Effect of IFN-β and IFN-γ, Alone and in Combination with H-7, on the Antigenic Phenotype of T47D Cells Applicants have previously demonstrated that both IFN-β and IFN-γ can effectively enhance the expression of BCA 225, HLA Class II antigens and ICAM-I expression in T47D cells [36]. Optimum enhancement was observed by 72 hr with ranges of interferon of 500 to 1000 units/ml of IFN-α or IFN-β and 50 to 500 units/ml of IFN-γ, in the presence or absence of 1.0 μg/ml of H-7, is shown in Tables 3 and 4. A higher dose of H-7 was employed in this study because the lower H-7 concentration of 0.1 μg/ml did not block enhanced antigenic expression in interferon treated T47D cells (data not shown). IFN-γ was more effective (even at lower concentrations) than IFN-β in enhancing the expression of BCA 225, HLA Class II antigens and ICAM-1. IFN-α also increased the expression of the three antigens tested, but to a lower extent than IFN-β or IFN-γ (data not shown). For example, in the experiment shown in Table 3, 500 units/ml of IFN-α enhanced HLA Class II expression from an MFI of 2,814 to an MFI of 11,660 (a 4-fold increase) as opposed to a 11- and a 69-fold increase, respectively, in HLA Class II expression in cells exposed to IFN-β or IFN-γ (data not shown). In a number of experiments, the de novo level of expression of specific antigens and the absolute level of upregulation varied. Part of this difference may reflect the use of a different FACS with different sensitivities for determining MFI units and/or innate differences in antigenic expression of cells as a consequence of the cell cycle. Although this makes it difficult to directly compare absolute levels of upregulation with the phorbol esters and ADMB versus the interferons, it still permits a comparison of the effect of H-7 on upregulation. In experiments simultaneously comparing the various compounds, IFN-γ was generally a more effective enhancer of HLA Class II antigens and ICAM-1 than the other agents, whereas MEZ was generally more effective in modifying c-erbB-2 and BCA 225 expression. Unlike antigenic upregulation induced by the phorbol esters and ADMB which was inhibited by H-7, even the higher dose of H-7 (1.0 μg/ml) did not inhibit the ability of IFN-β or IFN-γ to enhance BCA 225, HLA Class II antigens and ICAM-1 expression in T47D cells.

To determine if H-7 could inhibit the ability of interferon to enhance the synthesis or shedding of BCA 225 in T47D cells, cultures were grown for 72 hr in the presence of 500 units/ml of IFN-β or 50 units/ml of IFN-γ and in the presence or absence of 1 μg/ml of H-7 (Table 4). As had been observed for interferon enhanced expression of BCA 225, H-7 did not inhibit the synthesis or shedding of BCA 225 induced in T47D cells by interferon. These results demonstrate that the ability of TPA and MEZ versus IFN-β and IFN-γ to upregulate the synthesis, expression and shedding of BCA 225 may occur by different mechanisms.

Figure 2A:
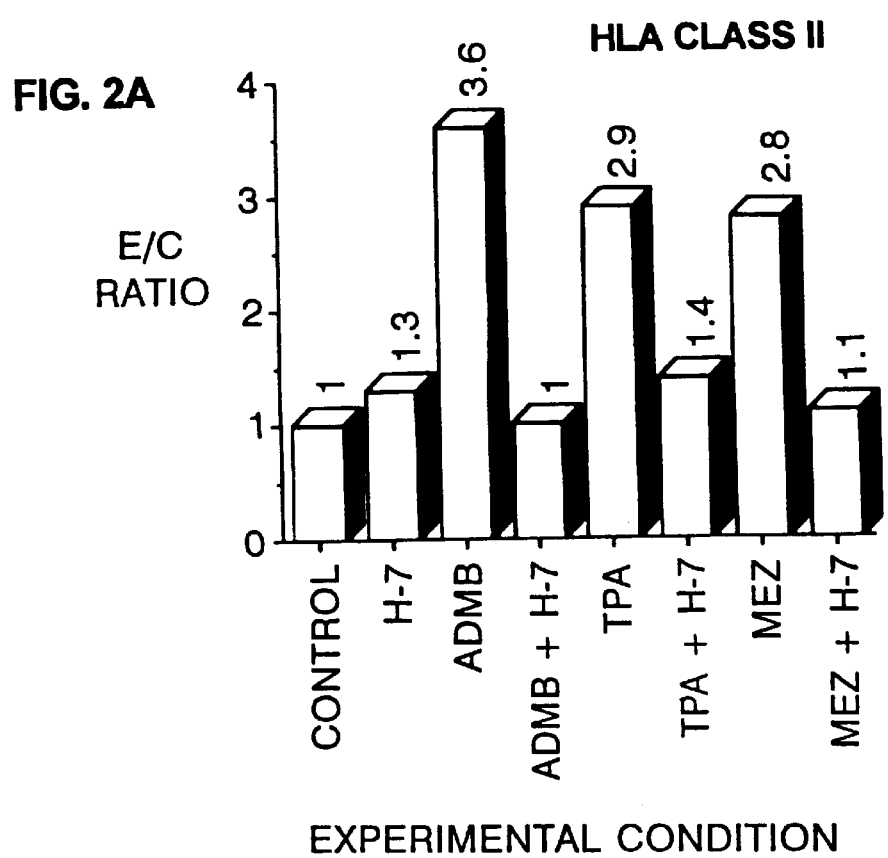
FIG. 2: Effect of H-7 on the upregulation of HLA Class II antigens-and c-erbB-2 antigen expression in T47D cells induced by ADMB, TPA and MEZ, T47D cells were grown for 72 hr in the presence of 0.1 $\mu$g/ml of ADMB, TPA or MEZ, used alone or in combination with 0.1 kg/ml of H-7. Cell surface antigen expression was then determined by FACS analysis as described in "Detailed Description Of The Invention." Base-line control antigen expression is given the value of 1.0. The values presented are the fold-change, which represents the ratio of the experimental MFI value versus the control MFI value for the specific antigen tested, in fluorescence in experimental versus control samples. The results presented are from a single experiment employing replicate samples. Similar results $\leq 15\%$ have been obtained in two additional studies. Further details can be found in "Detailed Description Of The Invention."
Figure 2B:
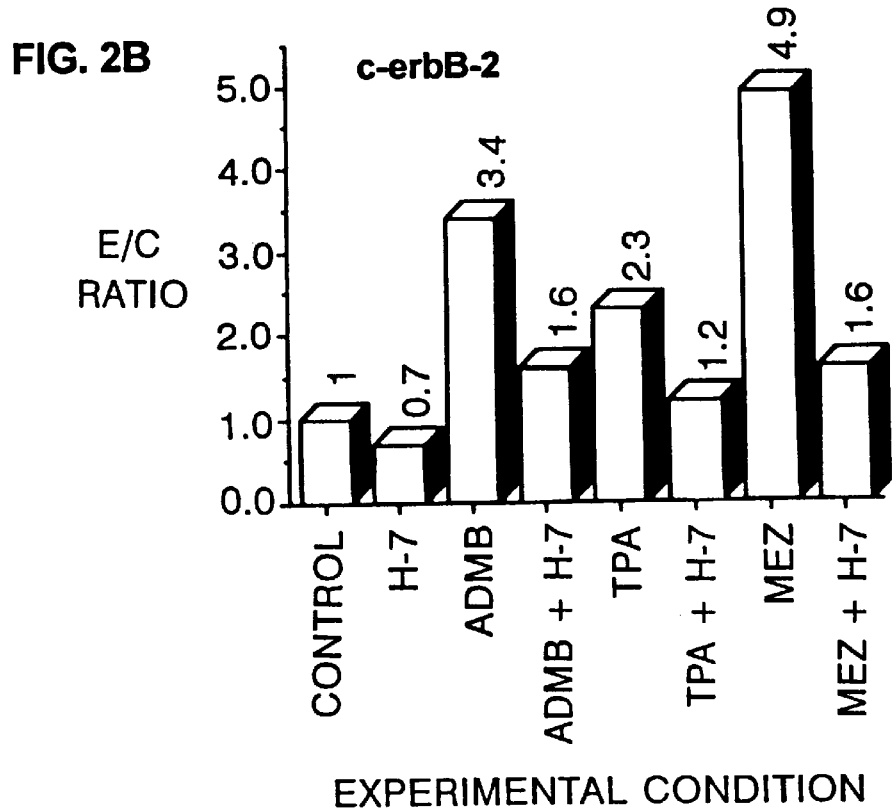
Figure 3:
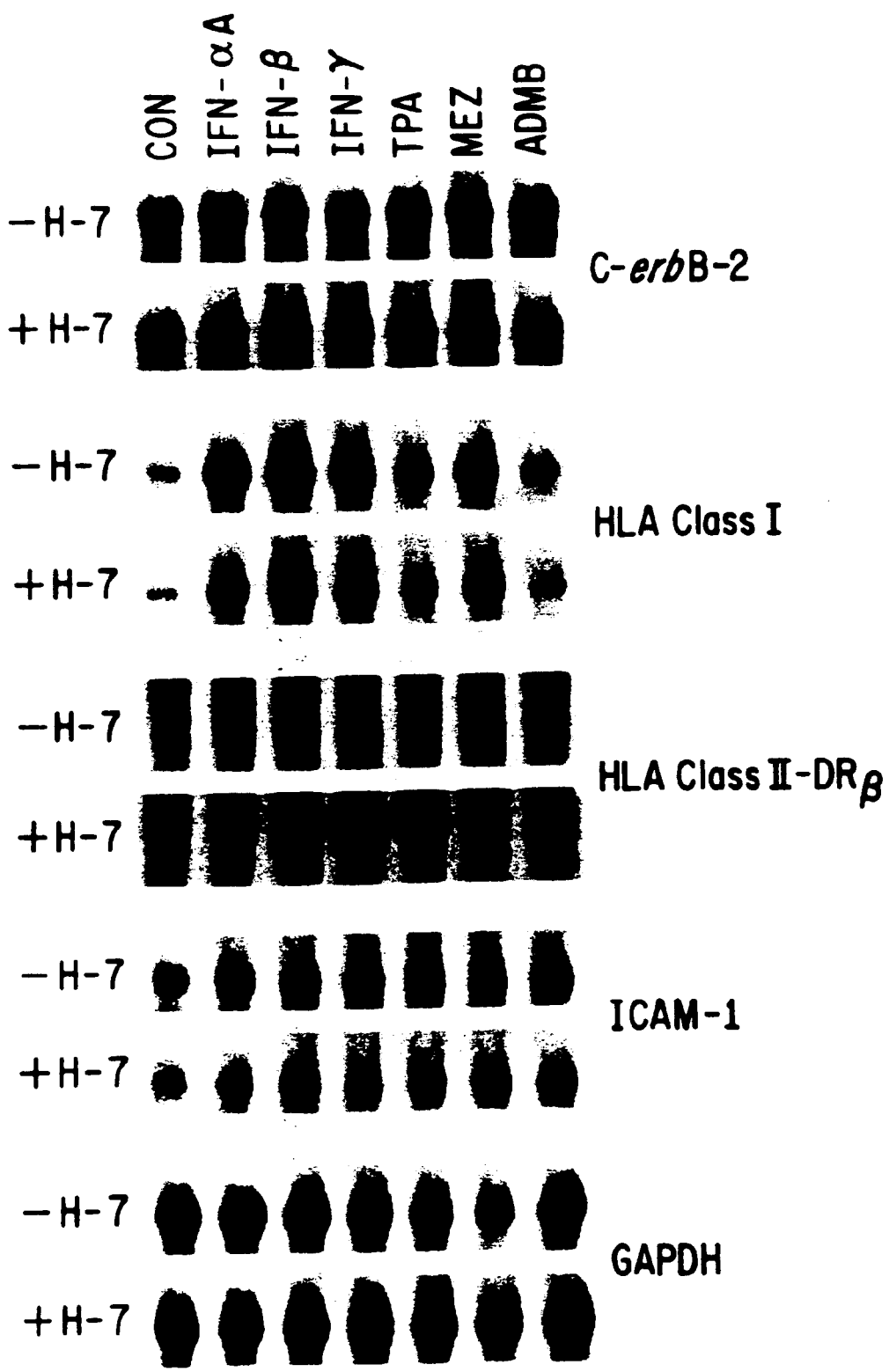
FIG. 3: Effect of interferon, ADMB, TPA and MEZ, alone and in combination with H-7, on steady-state mRNA levels of HLA Class I antigens, HLA Class II-DR$_\beta$ antigen, c-erbB-2, ICAM-1 and GAPDH in T47D human breast carcinoma cells. T47D cells were grown for 72 hr in the absence (control) or presence of 500 units/ml of IFN-α or IFN-β, 50 units/ml of IFN-γ, 0.1 $\mu$g/ml of TPA, MEZ or ADMB. Cultures were also grown in the presence of 0.1 $\mu$g/ml of H-7 for 72 hr with and without the additional compounds indicated above. Total cytoplasmic RNA was isolated and processed as described in "Detailed Description Of The Invention." Control: CON; recombinant human leukocyte interferon-A: IFN-αA; recombinant human fibroblast interferon: IFN-β; recombinant human immune interferon: IFN-γ; ADMB; 3-(N-acetylamino)-5-(N-decyl-N-methylamino)-benzyl alcohol; TPA; 12-0-tetradecanoyl-phorbol-13-acetate; MEZ; mezerein; H-7: (1-(5-isoquinolinesulfonyl)-2-methylpiperazine dihydrochloride.

Effect of ADMB, TPA, MEZ and Interferon, Alone and in Combination with H-7, on the Steady-State Levels of HLA Class I Antigens, HLA Class II-DRβ Antigen, ICAM-1 and c-erbB-2 in T47D Cells To determine if the increase in HLA Class II-DR$_β$ antigen, ICAM-1 and c-erbB-2 expression in T47D cells resulting from 72 hr ADMB, TPA, MEZ, IFN-α, IFN-β or IFN-γ treatment involved enhanced mRNA expression, the steady-state levels of mRNA for the respective genes were determined (FIG. 3). In the case of HLA Class II-DR antigen, small increases in mRNA levels were observed in IFN-α (1.1-fold), IFN-β (1.2-fold), IFN-γ (1.25-fold) and MEZ (1.2-fold) treated T47D cells. ADMB and TPA did not increase HLA Class II-DR$_β$ antigen, RNA expression, although ADMB was slightly more effective than MEZ in enhancing cell surface expression of this antigen in T47D cells (FIG. 2). MEZ and IFN-γ were the most effective enhancers of HLA Class II-DR$_β$ antigen mRNA expression, whereas IFN-γ was more effective than MEZ in enhancing expression of this antigen in T47D cells (Tables 1 and 3). When cotreated with the respective antigenic modulating compound and H-7, only minimal changes in HLA Class II-DR$_β$ antigen mRNA levels (<1.15-fold) were observed. These observations are in contrast to the HLA Class II-DR antigenic modulation induced by these agents in T47D cells. As described above, H-7 effectively blocked ADMB, TPA and MEZ enhancement of HLA Class II-DR antigen expression in T47D cells (Table 3). In the case of HLA class I antigen expression, mRNA levels were variably increased following treatment with IFN-α(1.9-fold), IFN-β (2.1-fold), IFN-γ(1.8-fold), TPA (1.3-fold) and MEZ (1.75-fold), whereas H-7 only marginally altered mRNA levels (≦1.2-fold) for this antigen (Table 3). With respect to surface expression, as observed with HLA Class II-DR antigen expression, H-7 inhibited upregulation induced by ADMB, TPA or MEZ, but not upregulation induced by the interferons (data not shown). These observations indicate that cell surface expression changes in both HLA Class I antigens and HLA Class II-DR antigen in T47D cells is not a consequence of a reduction in mRNA levels for these gene products. Further studies are required, however, to determine if the antigenic modulating agents, employed alone or in combination with H-7, modulate the rate of mRNA synthesis and/or decay of mRNA synthesis for HLA Class II-DR or HLA Class I antigens in T47D cells.

ICAM-1 mRNA levels were increased a maximum of only 1.3-fold after 72 hr treatment under the various experimental conditions and H-7 only modestly altered ICAM-1 expression (FIG. 3). In the case of c-erbB-2, a maximum increase of only 1.2-fold in the levels of mRNA were apparent after 72 hr treatment with the various agents. Similarly, no differential change in c-erbB-2 mRNA was observed in T47D cells grown in the presence of any of the antigenic modulating agents plus H-7. These results again contrast those measuring surface expression of these antigens. As demonstrated in Tables 1 and 3, H-7 partially inhibited enhanced ICAM-1 expression (Table 3). Similarly, H-7 inhibited enhanced surface expression of c-erbB-2 induced by ADMB, TPA and MEZ (FIG. 2 and Table 1), whereas it did not alter upregulation induced by the interferons (data not shown). These results provide further support for the lack of a direct correlation between the levels of ICAM-1 and c-erbB-2 mRNA and antigenic expression in cells treated with the combination of ADMB, TPA, MEZ or interferon and H-7. Further studies are required, however, to determine if the antigenic modulating agents, employed alone or in combination with H-7, modulate the rate of mRNA synthesis and/or decay of mRNA synthesis for ICAM-1 or c-erbB-2 in T47D cells.

Effect of 3-(N-acetylamino)-5-(N-decyl-N-methylamino)-benzyl Alcohol (ADMB), Mezerein (MEZ) and Recombinant Human Immune Interferon (IFN-1) on Antigen Expression in WiDr Human Colon Carcinoma Cells Monitored by Fluorescence Activated Cell Sorter (FACS) Analysis Cells were plated in 10 cm plates, media was changed 24 hours later with no addition (control) or addition of the indicated compounds and cells were incubated at 37° C. for the indicated time (72 or 96 hours). Cells were resuspended using 10× EDTA and antigen expression was determined as described (Leon, Mesa-Tejada, Gutierrez, Estabrook, Greiner, Schlom & Fisher: Anticancer Res. 9:1639–1648, 1989; Leon, Gutierrez, Jiang, Estabrook, Waxman & Fisher: Cancer Immunol. Immmunother. 35:315–324, 1992). The results of the experiments are presented in Table 5.

To summarize, Table 5 indicates: 1) class II HLA-DR antigens and the tumor associated antigen CA19.9 are elevated in WiDr human colon carcinoma cells treated for 72 or 96 hours with ADMB, MEZ or IFN-γ; 2) the order of effectiveness in increasing Class II HLA-DR antigens in WiDr cells is IFN-γ>MEZ>ADMB (IFN-γ is approximately 3× more active than ADMB); 3) with all three immuno-modulating agents (IFN-γ, MEZ and ADMB), 96 hour treatment is more effective than 72 hours in inducing elevated Class II HLA-DR and CA19.9 antigen expression; and 4) in the case of the TAA CA19.9, MEZ is more effective than IFN-γ or ADMB in increasing expression after 96 hours treatment.

Conclusion

ADMB, as well as two documented immunomodulating agents (IFN-γ and MEZ), can increase the surface expression of both Class II HLA-DR and the TAA CA19.9 in the human colon carcinoma cell line WiDr.

Effect of 3-(N-acetylamino)-5-(N-decyl-N-methylamino)-benzyl Alcohol (ADMB), Mezerein (MEZ) and Recombinant Human Immune Interferon (IFN-y) on Antigen Expression in CBS Human Colon Carcinoma Cells Monitored by Fluorescence Activated Cell Sorter (FACS) Analysis Cells were plated in 10 cm plates, media was changed 24 hours later with no addition (control) or addition of the indicated compounds and cells were incubated at 37° C. for 96 hours. Cells were resuspended using lOX EDTA and antigen expression was determined as described (Leon, Mesa-Tejada, Gutierrez, Estabrook, Breiner, Schlom & Fisher: Anticancer Res. 9:1639–1648, 1989; Leon, Gutierrez, Jiang, Estabrook, Waxman & Fisher: Cancer Immuno. Immunother. 35:315–324 1992). The results of the experiments are presented in Table 6.

To summarize, Table 6 indicates: 1) Class II HLA-DR antigens and the tumor associated antigen CA19.9 are elevated in CBS human colon carcinoma cells treated for 96 hours with ADMB, MEZ or IFN-γ; 2) the relative order of effectiveness in increasing Class II HLA-DR antigens in CBS cells is IFN-γ>MEZ>ADMB. (IFN-γ is approximately 2× more active than ADMB); and 3) ADMB is more effective than MEZ in enhancing CA19.9 TAA expression, but less effective than IFN-γ (Rank order of effectiveness IFN-γ>ADMB>MEZ).

Conclusion

ADMB, as well as two documented immunomodulating agents (IFN-γ and MEZ), can increase the surface expression of both Class II HLA-DR and the TAA Ca19.9 in the human colon carcinoma cell line CBS.

Summary Conclusion

ADMB can augment Class II HLA-DR antigen and CA19.9 TAA expression in human colon carcinoma cells (WiDr and CBS).

The data in Tables 5 and 6 demonstrate that ADMB can augment both Class II HLA-DR and TAA expression in two human colon carcinoma cell lines. It appears, therefore, that ADMB, and mechanistically similar compounds, should find utility in increasing HLA and TAA expression in both breast and colon carcinoma cells. Studies are continuing to determine if ADMB can stimulate antigenic expression in additional carcinomas.

EXPERIMENTAL DISCUSSION

Among the diversity of interferon effects on target cells, recent investigations have focused on the ability of these bioresponse modulators to enhance the expression of both histocompatibility antigens and TAAs in tumor cells (for review see [1,9,23,25,26]) These studies indicate that interferon may prove valuable in altering the phenotype of tumor cells rendering them more accessible to monoclonal antibody targeting [13,21,36,42]. A frequent observation is that interferon functions predominantly as an enhancer of antigenic expression, rather than an inducer of de novo expression of specific antigens [9,15,16,25,31]. At the present time, little information is available on the biochemical mechanisms underlying interferon upregulation of antigenic expression. Studies comparing the protein synthesis requirements for antigenic modulation induced by types I (IFN-α/β) and type II (IFN-γ) interferon in human melanoma cells suggest that different biochemical pathways mediate up-regulation of both major histocompatibility complex (MHC) and non-MHC encoded glycoproteins induced by these compounds [17]. IFN-γ enhancement of antigen expression depends on continued protein synthesis, whereas the modulatory effect of IFN-α and IFN-β can occur in the presence of the protein synthesis inhibitor cycloheximide. Numerous studies have also indicated that types I and II interferons can differ in their effects on TAA expression in the same tumor cell (for review see [1,23,25,48]). Both the absolute level of antigenic modulation induced by different interferons, as well as the type of effect elicited in specific target cells, i.e. either stimulatory or inhibitory, has been shown to vary (for review see [1,23]). In the present study applicants have addressed the potential relationship between PKC activation and antigenic modulation induced by recombinant IFN-β and IFN-γ in the human breast carcinoma cell line T47D. Since both TPA and MEZ can augment the expression of the same histocompatibility antigens and TAAs in T47D cells as recombinant interferons and these agents appear to work directly via activation of PKC (for review see [43,44]), applicants have also incorporated these agents in our studies.

The enhanced cellular antigenic expression induced in T47D cells by TPA, MEZ and ADMB was eliminated by simultaneous incubation with the PKC-inhibitor H-7. Similarly, the ability of TPA and MEZ to enhance the synthesis and shedding of the TAA BCA 225 was also blocked by H-7. In contrast, ADMB failed to induce increased shedding of BCA 225 by T47D cells, whereas it was similarly active as TPA in enhancing BCA 225 synthesis and expression (Table 2). These observations suggest that ADMB can differentially modify the antigenic phenotype in T47D cells in comparison with TPA and MEZ, i.e. it can augment synthesis and expression without enhancing shedding of specific TAAs. Interestingly, ADMB was found to induce HLA Class II antigens in a similar manner as TPA and MEZ in T47D cells. HLA Class II antigens have been shown to be involved in the differentiation of mammary epithelium [11] and they play a critical role in antigen presentation to T-cells [35], the transport of key intracellular peptides to the extracellular milieu [57] and recruitment of lymphoid cells to tumor cells [11,35,59]. The ability of ADMB to enhance both HLA Class II antigens and TAA expression on T47D cells could have implications with respect to the induction of an immune response to this tumor in vivo. A severe limitation preventing the use of TPA or MEZ as potential immunomodulators in humans is there well documented tumor promoting activity in the mouse skin two-stage carcinogenesis assay (for review see [51–52]). At the present time, ADMB has not been tested for in vivo toxicity, tumor promoting activity and/or in vivo immunomodulatory properties. However, it this compound can pass this scrutiny, it could prove useful as an antigenic modulating agent in situations where increased surface expression without a concomitant increase in TAA shedding is desired.

Previous studies have indicated a possible involvement of activation of PKC in the early events associated with IFN-α action in specific target cells [2,6,7,46,50,60–62]. Although not studied as extensively, an association between PKC activity and both IFN-β- and IFN-γ-induced cellular changes has also been suggested [8,29,30,45,47]. In addition, a differential role for PKC in IFN-α/β versus IFN-γ induced cellular and gene expression changes in the same target cell has also been observed [6,37,47]. Both IFN-β and IFN-γ produced similar antigenic changes in T47D cells as TPA and MEZ, including enhancing the shedding of BCA 225. However, up-regulation of antigen expression and increased shedding induced by IFN-β and IFN-γ was not inhibited by H-7 (Table IV). IFN-α was less effective than either IFN-β or IFN-γ in modifying the antigenic phenotype of T47D cells and its activity also was not blocked by H-7 (data not shown). These results suggest that the mechanism by which interferons modulate antigen expression in T47D cells occurs by a PKC-independent pathway. A similar dissociation between PKC activation and the ability of IFN-γ and TPA to induce specific antigenic expression changes in human keratinocyte cultures has recently been reported [24]. IFN-γ and TPA both enhanced ICAM-1 expression in human keratinocyte cultures and the enhancement effect of TPA, but not that of IFN-γ, was inhibited by H-7. Similarly, only IFN-γ induced HLA Class II-DR antigen expression in human keratinocytes and H-7 also failed to block this induction. Koide et al. [34] demonstrated that IFN-γ induction of HLA Class II-DR antigen expression in HL-60 cells also was not modified by H-7. In contrast, W7 (a calmodulin antagonist) blocked IFN-γ-induction of HLA Class II-DR expression in HL-60 cells supporting a possible involvement of calcium/calmodulin in antigenic modulation in this cell line. Similarly, treatment of murine macrophages with IFN-γ resulted in the induction of both increased mRNA and MHC I-$A_\beta$ antigen expression, and both of these parameters were unaltered in the presence of H-7 [5]. W-7 did, however, modify the MHC I-$A_\beta$ antigen MRNA induction process elicited by IFN-γ treatment in murine macrophages. In the case of the human melanoma cell line H0-1, the enhanced expression of HLA Class I antigens, HLA Class II antigens and ICAM-1 induced by IFN-γ was again only marginally affected by H-7 [26]. Since upregulation of antigen expression in T47D cells induced by PKC activators such as TPA, MEZ and ADMB are inhibited by H-7, whereas similar changes induced by the interferons are not blocked by H-7, these results further indicate that the mechanism controlling antigenic modulation in specific cell cultures is dependent on the specific inducer employed and antigenic modulation can occur by both a PKC-independent and a PKC-dependent pathway.

The mechanism by which ADMB and MEZ versus IFN-γ enhance the expression of specific cellular antigens and TAAs in T47D is not presently known. Analysis of steady state mRNA levels of HLA Class I, HLA Class II-$DR_\beta$, ICAM-1 and c-erbB-2 in cells treated with these different compounds indicated various levels of modulation which did not correlate directly with the relative level of change in surface expression of these antigens. Similarly, H-7 did not significantly alter the level of mRNA for the various antigens under any of the experimental conditions. These results suggest that the ability of H-7 to modulate the antigenic enhancing properties of ADMB, TPA, MEZ and the interferons may occur at a posttranscriptional level. Alternatively, these agents may modify antigenic expression by altering the rate of mRNA transcription and/or mRNA stability. In the case of BCA 225, H-7 may exert its suppressive effect on ADMB-, TPA-, and MEZ-induced increases in surface expression by inhibiting the ability of these compounds to enhance the synthesis of this TAA in T47D cells. Alternatively, H-7 might block antigenic upregulation in ADMB, TPA and MEZ treated cells by preventing the necessary biochemical alterations responsible for the insertion of the various antigens into the cell membrane in a form recognized by the monoclonal antibodies employed. Further studies are clearly required to determine the mechanism by which specific antigenic modulators upregulate antigen expression and the mechanism by which H-7 selectively inhibits this process in cells treated with ADMB, TPA or MEZ. The present model system should prove useful in determining the biochemical mechanism(s) underlying antigenic upregulation in response to diverse transmembrane signalling agents. With this information it may be possible in the future to design strategies and molecules specifically tailored to alter the antigenic phenotype of tumor cells making them more accessible to monoclonal antibody targeted therapeutic approaches.

TABLE 1

Effect of the PKC Inhibitor H-7 on Upregulation of HLA Class II antigens, c-erbB-2 and ICAM-1 by TPA and MEZ in T47D Human Breast Carcinoma Cells.

| Experimental Conditions[a] | Antigenic Expression (MFI) | | |
|---|---|---|---|
| | HLA Class II | c-erbB-2 | ICAM-1 |
| Control | 3,410 | 7,144 | 20,975 |
| H-7 | 4,563 | 7,045 | 21,538 |
| | (1.3)[b] | (1.0) | (1.0) |
| TPA | 9,984 | 16,100 | 63,175 |
| | (2.9) | (2.3) | (3.0) |
| TPA + H-7 | 4,778 | 8,385 | 47,542 |
| | (1.4) | (1.2) | (2.3) |
| MEZ | 10,260 | 18,385 | 85,745 |
| | (3.0) | (2.6) | (4.1) |
| MEZ + H-7 | 3,654 | Not Detected | 39,486 |
| | (1.1) | | (1.9) |

[a]T47D cells were grown for 72 hr in 0.1 μg/ml TPA or 0.1 μg/ml MEZ, in the presence or absence of 0.1 μg/ml H-7. Cells were resuspended, incubated with monoclonal antibodies specific for HLA Class II antigens, c-erbB-2 or ICAM-1 and anti-mouse FITC secondary antibody. Cells were then analyzed by flow cytometry using a FACStar (Beckon Dickinson, Mountain View, CA) and antigenic expression is expressed as mean fluorescence intensity (MFI) units. Further details can be found in "Detailed Description of the Invention."
[b]Numbers in brackets reflect the level of upregulation versus untreated control cells (equivalent to 1.0)

TABLE 2

Effect of the PKC Inhibitor H-7 on the Enhanced Synthesis, Expression and Shedding of BCA 225 Induced by TPA, MEZ and ADMB in T47D Human Breast Carcinoma Cells.

| Experimental Conditions[a] | BCA 225 Synthesis[b] (ng/mg protein) | BCA 225 Expression[c] (MFI) | BCA 225 Shedding[d] (ng/ml/10[6] cells) |
|---|---|---|---|
| Control | 164 | 6,426 | 28 |
| H-7 | 142 (0.9)[e] | 5,428 (0.8) | 23 (0.8) |
| TPA | 394 (2.4) | 11,696 (1.8) | 84 (3.0) |
| TPA + H-7 | 191 (1.2) | 7,434 (1.2) | 35 (1.3) |
| MEZ | 507 (3.1) | 16,065 (2.5) | 147 (5.3) |
| MEZ + H-7 | 225 (1.4) | 7,068 (1.1) | 39 (1.4) |
| ADMB | 299 (1.8) | 12,825 (2.0) | 26 (0.9) |
| ADMB + H-7 | 178 (1.1) | 7,018 (1.1) | 34 (1.2) |

[a]T47D cells were incubated for 72 hr in the presence of 0.1 μg/ml TPA, 0.1 μg/ml MEZ or 0.25 μg/ml ADMB, in the presence or absence of 0.1 μg/ml H-7.
[b]Cell lysates were prepared and BCA 225 levels were determined by double-determinant BCA 225 ELISA assay as described in "Detailed Description of the Invention."
[c]Membrane expression of BCA 225 was determined by flow cytometry using a FACStar (Beckon Dickinson, Mountain View, CA) with CU18 monoclonal antibodies as described in "Detailed Description of the Invention." The results are expressed as mean fluorescence intensity (MFI) units.
[d]The shedding of BCA 225 into the culture medium was calculated using a double-determinant BCA 225 ELISA procedure as described in "Detailed Description of the Invention."
[e]Values in brackets reflect the level of enhancement in BCA 225 relative to control (equivalent to 1.0)

TABLE 3

Effect of the PKC Inhibitor H-7 on Upregulation of HLA Class II antigens and ICAM-1 by IFN-β and IFN-γ in T47D Human Breast Carcinoma Cells.

| Experimental Conditions[a] | Antigenic Expression (MFI) | |
|---|---|---|
| | HLA Class II | ICAM-1 |
| Control | 2,919 | 54,536 |
| H-7 | 3,490 (1.2)[b] | 54,080 (1.0) |
| IFN-β | 31,413 (10.8) | 97,013 (1.8) |
| IFN-β + H-7 | 32,190 (11.1) | 108,902 (2.0) |
| IFN-γ | 202,102 (69.2) | 191,490 (3.5) |
| IFN-γ + H-7 | 210,812 (75.2) | 188,544 (3.5) |

[a]T47D cells were incubated for 72 in the presence of 500 units/ml IFN-β or 50 units/ml IFN-γ, in the presence or absence of 1.0 μg/ml of H-7. Cells were then incubated with Monoclonal Antibodies specific for HLA Class II antigens or ICAM-1 followed by fluorescinated anti-mouse IgG antibody and then analyzed by flow cytometry with a Coulter Epics IV FACS (Coulter Electronics, Hialeah, FL.) as described in "Detailed Description of the Invention." Results are expressed as mean fluorescence intensity (MFI) units.
[b]Values in brackets indicate the relative increase in expression versus untreated controls (equivalent to 1.0)

TABLE 4

Effect of the PKC Inhibitor H-7 on the Enhanced Synthesis, Expression and Shedding of BCA 225 Induced by IFN-β and IFN-γ in T47D Human Breast Carcinoma Cells.

| Experimental Conditions[a] | BCA 225 Synthesis[b] (ng/mg/protein) | BCA 225 Expression[c] (MFI) | BCA 225 Shedding[d] (ng/ml/10⁹⁶ cells) |
|---|---|---|---|
| Control | 223 | 2,816 | 47 |
| H-7 | 230 (1.0)[e] | 2,560 (0.9) | 38 (0.8) |
| IFN-β | 374 (1.7) | 5,716 (2.0) | 69 (1.5) |
| IFN-β + H-7 | 361 (1.6) | 5,714 (2.0) | 66 (1.4) |
| IFN-γ | 722 (3.2) | 9,069 (3.2) | 64 (1.4) |
| IFN-γ + H-7 | 694 (3.1) | 8,177 (2.9) | 64 (1.4) |

[a]T47D cells were incubated for 72 hr with 500 units/ml IFN-β or 50 units/ml of IFN-γ, in the presence or absence of 1.0 μg/ml of H-7.
[b]BCA 225 synthesis was calculated by ELISA using cell lysates as described in "Detailed Description of the Invention."
[c]BCA 225 cell surface expression was measured by flow cytometry using a FACStar (Beckon Dickinson, Mountain View, CA) as described in "Detailed Description of the Invention." Results are expressed as mean fluorescence intensity (MFI) units.
[d]Shedding of BCA 225 into the culture medium was measured by ELISA as described in "Detailed Description of the Invention."
[e]Values in brackets indicate the relative change in BCA 225 in comparison with controls (equivalent to 1.0).

TABLE 5

Effect of 3-(N-acetylamino)-5-(N-decyl-N-methylamino)-benzyl alcohol (ADMB), Mezerein (MEZ) and Recombinant Human Immune Interferon (IFN-γ) on Antigen Expression in WIDr Human Colon Carcinoma Cells Monitored by Fluorescence Activated Cell Sorter (FACS) Analysis

| Experimental Conditions[a] | Monoclonal Antibody Binding (MFI)[b] | | |
|---|---|---|---|
| | MoAb K56 | MoAb L243 (HLA-DR) | MoAb B67.4 (CA19.9) |
| 72 Hour Treatment | | | |
| Control | 840 | 342 | 1260 |
| ADMB (0.01 μg/ml) | 844 | 390 | 1136 |
| ADMB (0.1 μg/ml) | 715 | 317 | 1172 |
| ADMB (1.0 μg/ml) | 879 | 486* | 1400* |
| MEZ (100 ng/ml) | 964* | 1120* | 1914* |
| IFN-γ (100 U/ml) | 1046* | 1724* | 2271* |
| 96 Hour Treatment | | | |
| Control | 1018 | 492 | 1475 |
| ADMB (0.01 μg/ml) | 827 | 434 | 1512 |
| ADMB (0.1 μg/ml) | 1116 | 615* | 2028* |
| ADMB (1.0 μg/ml) | 1008 | 806* | 2417* |
| MEZ (100 ng/ml) | 1104 | 2129* | 4784* |
| IFN-γ (100 U/ml) | 1021 | 2376* | 3191* |

[a]Cells were plated in 10 cm plates, media was changed 24 hours later with no addition (control) or addition of the indicated compounds and cells were incubated at 37° C. for the indicated time (72 or 96 hours). Cells were resuspended using 10X EDTA and antigen expression was determined as described (Leon, Mesa-Tejada, Gutierrez, Estabrook, Greiner, Schlom & Fisher: Anticancer Res. 9: 1639–1648, 1989; Leon, Gutierrez, Jiang, Estabrook, Waxman & Fisher: Cancer Immunol. Immmunother. 35:315–324, 1992)
[b]Values presented represent mean fluorescence intensity units (MFI). MFI = (mean channel fluorescence in fluorescence positive antibody-binding cells x % of Fluorescence positive antibody-binding cells) − (mean channel fluorescence of unstained cells x % of fluorescence positive cells in the unstained population). The data presented reflects the average of duplicate samples per experimental point which varied by ≦ 10%. Antibodies used included: MoAb K56, MoAb L243 (recognizes HLA-DR) and MoAb B67.4 (recognizes the tumor associated antigen, CA19.9).
*Enhanced antigen expression.

TABLE 6

Effect of 3-(N-acetylamino)-5-(N-decyl-N-methylamino)-benzyl alcohol (ADMB), Mezerein (MEZ) and Recombinant Human Immune Interferon (IFN-γ) on Antigen Expression in WIDr Human Colon Carcinoma Cells Monitored by Fluorescence Activated Cell Sorter (FACS) Analysis

| Experimental Conditions[a] | Monoclonal Antibody Binding (MFI)[b] | | |
|---|---|---|---|
| | MoAb K56 | MoAb L243 (HLA-DR) | MoAb B67.4 (CA19.9) |
| Control | 2034 | 3941 | 1509 |
| ADMB (0.01 μg/ml) | 2126 | 4112 | 3562* |
| ADMB (0.1 μg/ml) | 1715 | 3328 | 3473* |
| ADMB (1.0 μg/ml) | 2420 | 6870* | 3962* |
| MEZ (100 ng/ml) | 3002* | 9726* | 3288* |
| IFN-γ (100 U/ml) | 3126* | 14972* | 4970* |

[a]Cells were plated in 10 cm plates, media was changed 24 hours later with no addition (control) or addition of the indicated compounds and cells were incubated at 37° C. for 96 hours. Cells were resuspended using 10X EDTA and antigen expression was determined as described (Leon, Mesa-Tejada, Gutierrez, Estabrook, Greiner, Schlom & Fisher: Anticancer Res. 9:1639–1648, 1989; Leon, Gutierrez, Jiang, Estabrook, Waxman & Fisher: Cancer Immunol. Immunother. 35:315–324 1992).
[b]Values presented represent mean fluorescence intensity units (MFI). MFI = (mean channel fluorescence in fluorescence positive antibody-binding cells C % of Fluorescence positive antibody-binding cells) − (mean channel fluorescence of unstained cells X % of fluorescence positive cells in the unstained population). The data presented reflects the average of duplicate samples per experimental point which varied by ≦ 10% Antibodies used included: MoAb K56, MoAb L243 (recognizes HLA-DR) and MoAb B67.4 (recognizes the tumor associated antigen, CA19.9).
*Enhanced antigen expression.

REFERENCES

1. Ahmed, M. A., Nielsch, U., Guarini, L., Hermo, H., Jr., Fisher, P. B. Modulation of differentiation: a potential mechanism by which interferons induce antitumor activity. In: Fisher, P.B., (ed.), *Mechanisms of differentiation: II Modulation of differentiation by exogenous agents* CRC Press, Boca Raton, p.1–56, (1990).

2. Akai, H., Larner, A. Phorbol ester-mediated down-regulation of an interferon-inducible gene, *J. Bio. Chem.*, 264:3252 (1989).

3. Babiss, L. E., Young, C. S. H., Fisher, P. B., Ginsberg, H. S. Expression of adenovirus E1A and E1B gene products and the *Escherichia coli* XGPRT gene in KB cells, *J. Virol.*, 46:454 (1983).

4. Blazar, B. A., Sutton, L. M., Strome, M. Self-stimulating growth factor production by B-cell lines derived from Burkitt's lymphomas and other cell lines transformed in vitro by Epstein-Barr virus. *Cancer Res.*, 43:4562 (1983).

5. Celada, A., Maki, R. A. IFN-γ induces the expression of the genes for MHC Class II I-$A_\beta$ and tumor necrosis factor through a protein kinase C-independent pathway, *J. Immunol.*, 146:114 (1991).

6. Csermely, P., Balint, E., Grimley, P. M., Aszalos, A. Protein kinase C is involved in the early signals of interferon-α but not interferon-γ in U937 cells, *J. Interferon Res.*, 10:605 (1990).

7. Faltynek, C. R., Princler, G. L., Gusella, G. L., Varesio, L., Radzioch, D. A functional protein kinase C is required for induction of 2–5A synthetase by recombinant interferon-αA in Daudi cells, *J. Biol. Chem.*, 264:14305 (1989).

8. Fan, X.-D., Goldberg, M., Bloom, B. R. Interferon-γ-induced transcriptional activation is mediated by protein kinase, C., *Proc. Natl. Acad. Sci. USA*, 85:5122 (1988).

9. Fisher, P. B., Rowley, P. T. Regulation of growth, differentiation and antigen expression in human tumor cells by recombinant cytokines: applications for the differentiation therapy of human cancer. In: Waxman, S., Rossi, G. B., and Takaku, F. (eds.) Status of differentiation therapy, Vol. II, Raven Press, New York, pp. 201–213 (1991).

10. Fisher, P. B., Schachter, D., Mufson, R. A, Huberman, E. The role of membrane lipid dynamics and translocation of protein kinase C in the induction of differentiation in human promyelocytic leukemic cells. In: Kabara JJ (ed.) Pharmacological effect of lipids: III. role of lipids in cancer research, The American Oil Chemists' Society, Champaign, Ill., pp. 69–89 (1989).

11. Forsum, U., Claesson, K., Mjelm, E., Karlsson-Parra, A., Klareskog, L., Scheynius, A., Tjernlund, U. Class II transplantation antigens: distribution in tissues and involvement in disease, *Scand. J. Immunol.*, 21: 389 (1985).

12. Fort, P., Marty, L., Piechaczyk, M., Sabrouty, S. E., Dani, C., Jeanteur, P., Blanchard, J. M. Various rat adult tissues express only one major mRNA species from the glyceraldehyde-3-phosphate-dehydrogenase multigenic family, *Nucleic Acids Res.*, 13: 1431 (1985).

13. Fuith, L. C., Marth, C., Muller-Holzner, E., Zechmann, W., Daxenbichler, G. Enhancement of CA 125 expression by interferon-gamma in ovarian carcinoma xenografts, *J. Tumor Marker Oncology*, 6: 85 (1991).

14. Giacomini, P., Aguzzi, A., Pestka, S., Fisher P. B., Ferrone, S. Modulation by recombinant DNA leukocyte (α) and fibroblast (β) interferons of the expression and shedding of HLA and tumor associated antigens by human melanoma cells, *J. Immunol.*, 133: 1649 (1984).

15. Giacomini, P., Fisher, P. B., Duigou, G. J., Gambari, R., Natali, P. G. Regulation of class II MHC gene expression by interferons: insights into the mechanism of action of interferon, *Anticancer Res.*, 8: 1153 (1988).

16. Giacomini, P., Fraioli, R., Nistico, P., Tecce, R., Nicotra, M. R., Di Filippo, F., Fisher, P. B., Natali, P. G. Modulation of the antigenic phenotype of early-passage human melanoma cells derived from multiple autologous metastases by recombinant human leukocyte, fibroblast and immune interferon, *Int. J. Cancer*, 46: 539 (1990).

17. Giacomini, P., Tecce, R., Sacchi, A., Fisher, P. B., Natali, P. G. Recombinant human IFN-γ, but not IFN-α or IFN-β, enhances MHC and non MHC encoded glycoproteins by a protein synthesis dependent mechanism, *J. Immunol.*, 140:3073 (1988).

18. Graham, G. M., Guarini, L., Moulton, T. A., Datta, S., Ferrone, S., Giacomini, P., Kerbel, R. S., Fisher, P. B. Potentiation of growth suppression and modulation of the antigenic phenotype in human melanoma cells by the combination of recombinant human fibroblast and immune interferons, *Cancer Immunol. Immunother.*, 32: 382 (1991).

19. Gray, P. W., Leung, B., Pennica, D., Yelverton, E., Najarian, R., Simonsen, C. C., Derynk, R., Sherwood, P. J., Wallace, D. M., Berger, S. L., Levinson, A. D., Goeddel, D. V. Expression of human immune interferon cDNA in *E. coli* and monkey cells, *Nature*, 295:502 (1982).

20. Greiner, J. W., Fisher, P. B., Pestka, S., Schlom, J. Differential effects of recombinant human leukocyte interferons on cell surface antigen expression, *Cancer Res.*, 46:4894 (1986).

21. Greiner, J. W., Guadagni, F., Noguchi, P., Pestka, S., Colcher, D., Fisher, P. B., Schlom. J. Use of recombinant interferon to enhance monoclonal antibody-targeting of carcinoma lesions in vivo, *Science*, 235: 895 (1987).

22. Greiner, J. W., Hand, P. H., Noguchi, P., Fisher, P. B., Pestka, S., Schlom, J. Enhanced expression of surface tumor-associated antigens on human breast and colon tumor cells after recombinant leukocyte α-interferon treatment, *Cancer Res.*, 44: 3208 (1984).

23. Greiner, J. W., Schlom, J., Pestka, S., Langer, J. A., Giacomini, P., Kusama, M., Ferrone, S., Fisher, P. B. Modulation of tumor associated antigen expression and shedding by recombinant human leukocyte and fibroblast interferons, *Pharmacol. Therapeut.*, 31:209 (1985).

24. Griffiths, C. E. M., Esmann, J., Fisher, G. J., Voorhees, J. J., Nickoloff, B. J. Differential modulation of keratinocyte intercellular adhesion molecule-1 expression by gamma interferon and phorbol ester: evidence for involvement of protein kinase C signal transduction, *British J. Dermatology*, 122:333 (1990).

25. Guadagni, F., Kantor, J., Schlom, J., Greiner, J. W. Regulation of tumor antigen expression by recombinant interferons, In: Fisher, P. B. (ed.), Mechanisms of differentiation: II. modulation of differentiation by exogenous agents, CRC Press, Boca Raton, pp. 57–80 (1990).

26. Guarini, L., Graham, G. M., Jiang, H., Ferrone, S., Zucker, S., Fisher, P. B. Modulation of the anitigenic phenotype of human melanoma cells by differentiation-inducing and growth-suppressing agents, *Pigment Cell Res. Suppl.*, 2:123–131 (1992).

27. Guarini, L., Temponi, M., Bruce, J. N., Bollon, A. P., Duigou, G. J., Moulton, T. A., Ferrone, S., Fisher, P. B. Expression and modulation by cytokines of the intercellular adhesion molecule-1 (ICAM-1) in human central nervous system tumor cell cultures, *Int. J. Cancer*, 46:1041 (1990).

28. Guarini, L., Temponi, M., Edwalds, G. M., Vita, J. R., Fisher, P. B., Ferrone, S. In vitro differentiation and antigenic changes in human melanoma cell lines, *Cancer Immunol. Immunother.*, 30:262 (1989).

29. Hamilton, T. A., Becton, D. L., Somer, S. D., Gray, P. W., Adams, D. O. Inteferon-γ modulates protein kinase C activity in murine peritoneal macrophages, *J. Biol. Chem.*, 260:1378 (1985).

30. Ito, M., Takami, Y., Tanabe, F., Shigeta, S., Tsukui,K., Kawade, Y. Modulation of protein kinase C activity during inhibition of tumor growth by IFN-β and IFN-γ, *Biochem. Biophys. Res. Commun.*, 150:126 (1988).

31. Kantor, J., Tran R., Greiner, J., Pestka, S., Fisher, P. B., Schlom, J. Modulation of carcinoembryonic antigen messenger RNA levels in human colon carcinoma cells by recombinant human γ-interferon, *Cancer Res.*, 49:2651 (1989).

32. Keydar, I., Ohno, T., Nayak, T., Sweet, R., Simoni, F., Weiss, F., Karby, S., Mesa-Tejada, R., Spiegelman, S. Properties of retrovirus-like particles produced by a human breast carcinoma cell line: immunologic relationship with mouse mammary tumor virus proteins, *Proc. Natl. Acad. Sci.*, 81:4188 (1984).

33. Klareskog, L., Forsum, U., Peterson, P. A. Hormonal regulations of the expression of Ia antigens on mammary gland epithelium, *Eur. J. Immunol.*, 10: 958 (1985).

34. Koide, Y., Ina, Y., Nezu, N., Yoshida, T. O. Calcium influx and $Ca^{2+}$-calmodulin complex are involved in interferon-γ-induced expression of HLA Class II molecules on HL-60 cells, *Proc. Natl. Acad. Sci.*, 85:3120 (1988)

35. Landei, M., Lamb, J. R., Bottazo, G. F., Feldman, M. Epithelial cells expressing aberrant MHC Class II determinants can present antigen to cloned human T-cells, *Nature*, 312:639 (1984).

36. Leon, J. A., Mesa-Tejada, R., Gutierrez, M. C., Estabrook, A., Greiner, J. W., Schlom, J., Fisher, P. B. Increased surface expression and shedding of tumor associated antigens by human breast carcinoma cells treated with recombinant human interferons or phorbol ester tumor promoters, *Anticancer Res.*, 9:1639 (1989).

37. Lew, D. J., Decker, T., Darnell, J. E., Jr. Alpha interferon and gamma interferon stimulate transcription of a single gene through different signal transduction pathways, *Mol. Cell. Biol.*, 9:5405 (1989).

38. Maio, M., Gulwani, B., Langer, J. A., Kerbel, R. S., Duigou, G. J., Fisher, P. B., Ferrone, S. Modulation by interferons of HLA antigens, high molecular weight-melanoma associated antigens and intercellular adhesion molecule-1 expression by cultured melanoma cells with different metastatic potential, *Cancer Res.*, 49:2980 (1989).

39. Mark, D. V., Lu, S. D., Creasey, A., Yamamoto, R., Lin, L. Site-specific mutagenesis of the human fibroblast interferon gene, *Proc. Natl. Acad. Sci. USA*, 81:5662 (1984).

40. Matsui, M., Temponi, M., Ferrone, S. Characterization of a monoclonal antibody-defined human melanoma-associated antigen susceptible to modulation by immune interferon, *J. Immunol.*, 139:2088 (1987).

41. Mesa-Tejada, R., Palakodety, R. B., Leon, J. A., Khatcherian, A. O., Greaton, C. J. Immunocytochemical distribution of a breast carcinoma associated glycoprotein identified by monoclonal antibodies, *Amer. J. Pathol.*, 130:305 (1988).

42. Murray, J. L., Zukiwski, A. A., Mujoo, K. M. Rosenblum, M.G. Recombinant α-interferon enhances tumor targeting of an antimelanoma monoclonal antibody in vivo, *J. Biol. Resp. Mod.*, 9:556 (1990).

43. Nishizuka, Y. J. Studies and perspectives of protein kinase C, *Science*, 233:305 (1986).

44. Nishizuka, Y. J. The molecular heterogeneity of protein kinase C and its implications for cellular regulation, *Nature*, 334:661 (1988).

45. Ostrowski, J., Meier, K. E., Stanton, T. H., Smith, L. L., Bomsztyk, K. Interferon-γ and interleukin-1α induce transient translocation of protein kinase C activity to membranes in a B lymphoid cell line, *J. Biol. Chem.*, 263:13786 (1988).

46. Pfeffer, L. M., Strulovici, B., Saltiel, A. R. Interferon-α selectively activates the β isoform of protein kinase C through phosphatidylcholine hydrolysis, *Proc. Natl. Acad. Sci. USA*, 87:6537 (1990).

47. Razdioch, D., Varesio, L. Protein kinase C inhibitors block the activation of macrophages by IFN-β but not by IFN-γ, *J. Immunol.*, 140:1259 (1988).

48. Reddy, P. G., Graham, G. M., Datta, S., Guarini, L., Moulton, T. A., Jiang, H., Gottesman, M. M., Ferrone, S., Fisher, P. B. Effect of recombinant fibroblast interferon and recombinant immune interferon on growth and the antigenic phenotype of multidrug-resistant human glioblastoma multiforme cells, *J. Natl. Cancer Inst.*, 83:1307 (1991).

49. Rehberg, E., Kelder, B., Hoal, E. G., Pestka, S. Specific molecular activities of recombinant and hybrid leukocyte interferons, *J. Biol Chem.*, 257:11497 (1982).

50. Reich, N. C., Pfeffer, L. M. Evidence for involvement of protein kinase C in the cellular response to interferon α, *Proc. Natl. Acad. Sci. USA*, 87:8761 (1990).

51. Slaga, T. J., Fischer, S. M., Nelson, K., Gleason, G. L. Studies on the mechanism of skin tumor promotion: evidence for several stages in promotion, *Proc. Natl. Acad. Sci. USA*, 77:3659 (1980).

52. Slaga, T. J., Sivak, A. W., Boutwell, R. A. (eds.) Carcinogenesis:A Comprehensive Survey, Vol. 2, Raven Press, New York (1978).

53. Staehlin, T., Hobbs, D. S., Kung, H.-F., Pestka, S. Purification of recombinant human leukocyte interferon (IFNrA) with monoclonal antibodies, *Meth. Enzymol.*, 78:505 (1981).

54. Su, Z.-Z., Fisher, P. B. Enhancement of oncogene-mediated Transformation in cloned rat embryo fibroblast (CREF) cells by 3-aminobenzamide. In: Pairier G. L. and Moreau P. (eds.), ADP-Ribosylation Reactions, Springer-Verlag, NY, pp. 203–210 (1992).

55. Su, Z.-Z., Fisher, P. B. Early events in methyl methanesulfonate enhancement of adenovirus transformation of cloned rat embryo fibroblast cells, *Mol. Carcinogenesis*, 2:252 (1989).

56. Su, Z.-Z., Grunberger, S., Fisher, P. B. Suppression of adenovirus type 5 E1A-mediated transformation and expression of the transformed phenotype by caffeic acid phenethyl ester (CAPE), *Mol. Carcinogenesis*, 4:231 (1991).

57. Unanue, E. R., Allen P. M. Comment on the finding of Ia expression in nonlymphoid cells, *Lab Invest.*, 55:123 (1986).

58. Wender, P. A., Konrad, F. K., Sharkey, N. A., Dell'Aquila, M. L., Blumberg, P. M. Analysis of the phorbol ester pharmacophore on protein kinase C as a guide to the rational design of new classes of analogs, *Proc. Natl. Acad. Sci. U.S.A.*, 83:4214 (1986).

59. Whitwell, H. L., Hughes, H. P. A., Moore, M., Ahmed, A. Expression of major histocompatibility antigens and leucocyte infiltration in benign and malignant human breast disease, *British J. Cancer*, 49:161 (1984).

60. Yan, C., Sehgal, P. B., Tamm, I. Signal transduction pathways in the inductuion of 2',5'-oligoadenylate synthetase gene expression by interferon α/β, *Proc. Natl. Sci. U.S.A.*, 86:2243 (1989).

61. Yap, W. H., Teo, T. S., Tan, T. H. An early event in the interferon-induced transmembrane signalling process, *Science,* 234:355 (1986).

62. Yap, W. H., Teo, T. S., McCoy, E., Tan, Y. H. Rapid and transient rise in diacylglycerol concentration in Daudi cells exposed to interferon, *Proc. Natl. Sci. Acad. Sci. U.S.A.,* 83:7765 (1986).

What is claimed is:

1. A method of detecting tumor cells comprising contacting tumor cells with an effective amount of a protein kinase C activator for the upregulation of expression of cell antigens of tumor cells, without inducing antigen shedding, and detecting the presence of said antigen.

2. The method of claim 1, wherein the protein kinase C activator is a synthetic protein kinase C activator.

3. The method of claim 2, wherein the protein kinase C activator is 3-(N-acetylamino)-5-(N-decyl-N-methylamino)-benzyl alcohol.

4. The method of claim 1, wherein the cell antigen is selected from a group consisting of a tumor associated antigen, a cell surface antigen, and a histocompatibility antigen.

5. The method of claim 4, wherein the tumor of the tumor associated antigen is a breast carcinoma.

6. The method of claim 4, wherein the tumor of the tumor associated antigen is a colon carcinoma.

7. The method of claim 5, wherein the tumor associated antigen is selected from a group consisting of BCA 225, carcinoembryonic antigen, and c-erb B2.

8. The method of claim 5, wherein the antigen is the cell surface antigen intercellular adhesion molecule-1.

9. The method of claim 3, wherein the effective amount is from about 0.01 $\mu$g/ml to about 10 $\mu$g/ml.

10. The method of claim 4, wherein the antigen is associated with a breast or colon carcinoma and is selected from a group consisting of a histocompatability antigen, Class II HLA-DR, and CA19.9.

* * * * *